Dec. 24, 1940. C. E. DOWNING Plant Pat. 436
LILY
Filed Jan. 9, 1940
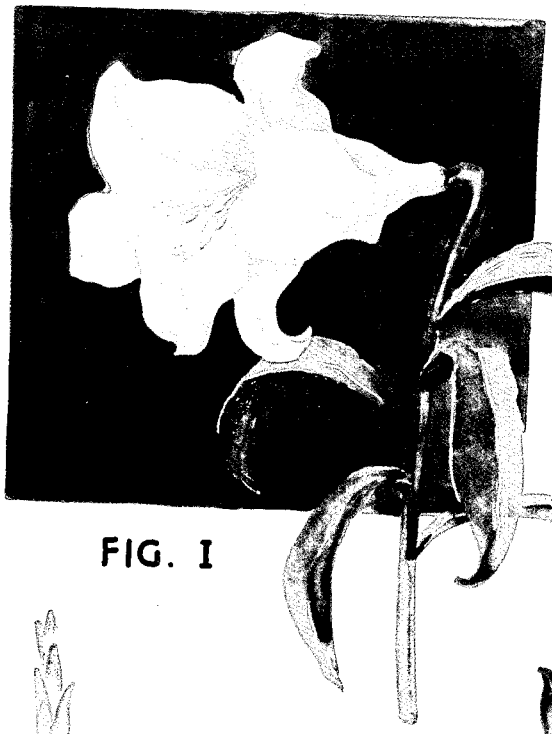
FIG. I
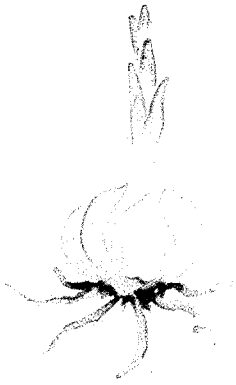
FIG. II
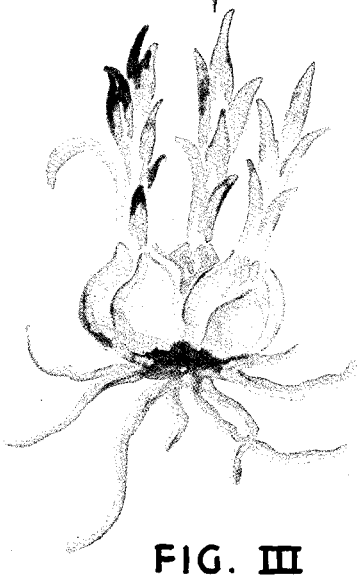
FIG. III
Inventor,
Clarence E. Downing,
by Frank S. Ashleman,
attorney.

Patented Dec. 24, 1940

Plant Pat. 436

UNITED STATES PATENT OFFICE

436

LILY

Clarence E. Downing, Sunfield, Mich.

Application January 9, 1940, Serial No. 313,129

1 Claim. (Cl. 47—60)

My new variety of lily is an improvement over all other forcing Easter lilies of the *longiflorum* type in that it has hardiness and successfully adapts itself to the severe climatic field conditions found in the North Central and Northern States. Forcing lilies are those types of lilies which may be brought into flower under glass at any time of the year, and have no dormant period.

It is the main object of my invention to produce a new variety of lily of the forcing type and habit that is hardy, and of which the bulbs may be successfully and commercially produced in the North and North Central part of the United States under field conditions. It is also my object to improve the form of the plant and flowers.

Flowers in my new variety of forcing lily are pure white inside and out, except in the throat of the calyx. The throat is new and different from all other forcing lilies in that it is a light canary yellow overlaid and diffused with emerald green. Light mixes the colors to the extent that the yellow nearly disappears.

In the illustration of the plant forming part of this specification:

Figure 1 illustrates the actual leaf foliage and flower in which one leaf is shown well up on the stem near the flower;

Figure 2 illustrates a year old bulb from bulblet with one stem; and

Figure 3 illustrates a two year old bulb from bulblet with three stems.

Another novel and new characteristic of my new forcing lily as asexually reproduced is its growing stem habit. Stems or crowns increase in number from the bulb each season, as shown by Fig. 2 which is a year old bulb from bulblet with one stem, and Fig. 3 which is a two year old bulb from bulblet with three stems. The crowns split apart and form new bulbs, thus making rapid propagation of my new forcing lily possible. In this manner only (from bulbs and attached bulblets) will the flower come true.

Another improved feature of my new forcing lily is its leaf foliage. The leaves are more numerous, wider, more curved and reach lower down on the stem, thus adding to the attractiveness of the plant. Fig. 1 illustrates the actual leaf foliage and flower; one leaf grows well up on the stem near the flower.

The herein described new lily was produced, as follows: First, the pollen of *Lilium regal* was placed on a receptive stigma of *Lilium longiflorum*, variety *giganteum*. Next, the pollen of *Lilium regal* was again placed on a receptive stigma of the issue of the first developed above described cross. My new variety of lily is an individual selection resulting from the above two crosses after careful and extensive testing under open field and under glass conditions.

The above described crosses were sought and perfected to obtain and combine the hardy characteristics of the *Lilium regal* and the forcing characteristics of the *Lilium longiflorum*. The result is my new variety which is a new forcing lily with hardy characteristics and other above described distinguishing new features. The double cross was necessary on account of the dominant characteristics of the female *Lilium longiflorum*.

My new described lily is distinguished from sterile Regal Lily, Plant Patent 165, in that it is a forcing lily with a practically entire white flower, and is of a multiple bulb character.

The following is a detailed description of my new lily:

Bulb: The bulb of my new lily, which is yellow, consists of large fleshy overlapping scales with one or more crowns, according to age of the bulb, as per Fig. 2 and Fig. 3.

Leaves: Numerous leaves, closely set on stem, about one inch wide, seven inches long, recurving, medium green color and shiny on upper side. The leaves are set well down to the base of the stem.

Flower: Flowers on my new lily are large and trumpet shaped, length six to seven inches, about the same distance in width or across face of flower. Petals are pure waxy white, except some green and yellow shading inside near the base of the midrib and the outer tips of the outer side segments of the flower. Inside segments are about two inches wide. Outer segments are rather narrow more like the *regal* than *longiflorum*, wavy and turning back along their sides and recurved at their tips.

That these new characteristics represented and explained actually represent a distinct and new reproducible variety is evidenced by the fact that all bulblets developed to the flowering stage have uniformly produced flowers having the same characteristics described and claimed herein.

What I claim as new and wish to secure by Letters Patent is:

The variety of lily of the *longiflorum* type characterized by the fact that the bulb splits readily to form several crowns permitting rapid propagation under commercial culture, and having stems varying in height from 18 to 24 inches and which is commercially cultured and is not injured by temperatures as low as —22° F. and furthermore having the characteristics of superior hardiness and therefore being more valuable for forcing purposes than other clons.

CLARENCE E. DOWNING.